US006685744B2

(12) United States Patent
Gellman et al.

(10) Patent No.: US 6,685,744 B2
(45) Date of Patent: Feb. 3, 2004

(54) EXPANDABLE URETERAL STENT

(75) Inventors: Barry N. Gellman, North Easton, MA (US); Benjamin Bottcher, Kennesaw, GA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 3 days.

(21) Appl. No.: 10/100,335

(22) Filed: Mar. 18, 2002

(65) Prior Publication Data

US 2003/0176831 A1 Sep. 18, 2003

(51) Int. Cl.[7] .................................................. A61F 2/36
(52) U.S. Cl. .................................... 623/23.66; 604/8
(58) Field of Search ....................... 604/8; 623/23.7, 623/23.66, 23.64

(56) References Cited

U.S. PATENT DOCUMENTS

| | | | |
|---|---|---|---|
| 4,787,884 A | 11/1988 | Goldberg | |
| 4,790,810 A | 12/1988 | Pugh, Jr. et al. | 604/8 |
| 4,813,925 A | 3/1989 | Anderson, Jr. et al. | 604/8 |
| 5,176,625 A | 1/1993 | Brisson | 604/8 |
| 5,372,600 A | 12/1994 | Beyar et al. | 606/108 |
| 5,380,270 A * | 1/1995 | Ahmadzadeh | 604/9 |
| 5,554,181 A | 9/1996 | Das | 623/1 |
| 5,647,843 A | 7/1997 | Mesrobian et al. | 604/8 |
| 5,681,274 A | 10/1997 | Perkins et al. | 604/8 |
| 5,766,209 A | 6/1998 | Devonec | 604/8 |
| 5,817,100 A | 10/1998 | Igaki | 606/108 |
| 5,964,744 A | 10/1999 | Balbierz et al. | |
| 5,964,771 A | 10/1999 | Beyar et al. | 606/108 |
| 6,090,115 A | 7/2000 | Beyar et al. | 606/113 |
| 2001/0053936 A1 * | 12/2001 | Whitmore | 623/23.7 |
| 2002/0183852 A1 * | 12/2002 | McWeeney | 623/23.7 |
| 2003/0069552 A1 * | 4/2003 | O'Keefe | 604/278 |

FOREIGN PATENT DOCUMENTS

| | | | |
|---|---|---|---|
| EP | 0365269 | * | 10/1989 |
| EP | 0806189 | | 11/1997 |
| WO | WO 00 66032 | | 11/2000 |
| WO | WO 01 91668 | | 12/2001 |

OTHER PUBLICATIONS

Int'l Search Report for Int'l Application No. PCTUS03/07023, dated Mar. 7, 2003, 6 pages.
Mardis et al., "Polyethylene Double–Pigtail Ureteral Stents," *Urologic Clinics of North America*, vol. 9, No. 1 (Feb. 1982).
Hepperlen et al., "Self–Retained Internal Ureteral Stents: A New Approach," The Journal of Urology, Copyright © 1978 by The Williams & Williams Co., vol.. 119, Jun.
Collier et al., "Proximal Stent Displacement As Complication of Pigtail Ureteral Stent," *Urology*, vol. XIII, No. 4 (Apr. 1979).

* cited by examiner

*Primary Examiner*—Corrine McDermott
*Assistant Examiner*—Thomas J Sweet
(74) *Attorney, Agent, or Firm*—Testa, Hurwitz & Thibeault, LLP

(57) ABSTRACT

An expandable ureteral stent placed in a patient's ureter so as to extend into the bladder of the patient. Expansion and contraction of the stent accommodates motion of the patient's kidney and bladder, gently holding the stent in position and reducing patient discomfort. The length of the stent is variable up to several centimeters.

35 Claims, 10 Drawing Sheets

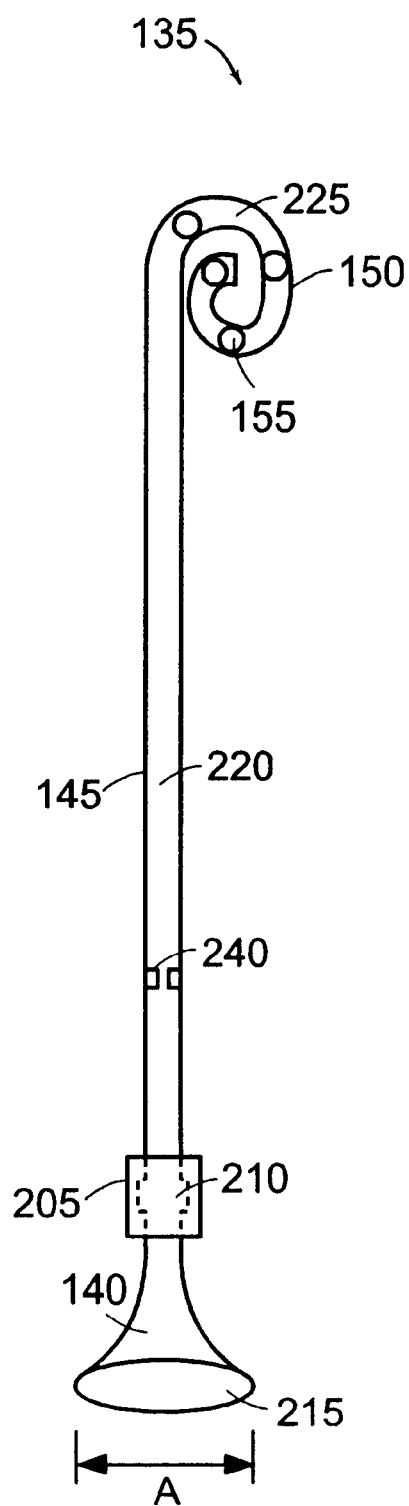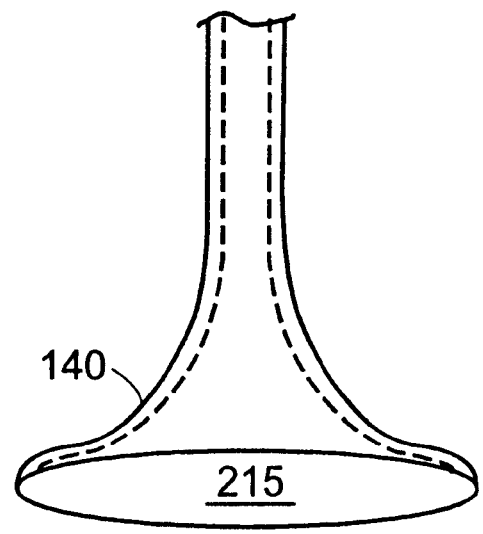
FIG. 2A
FIG. 2B

EXPANDABLE URETERAL STENT

FIELD OF THE INVENTION

This invention relates generally to medical devices for the drainage of fluids, and more specifically to ureteral stents.

BACKGROUND OF THE INVENTION

A ureter is a tubular passageway in a body that conveys urine from a kidney to a bladder. Urine is transported through the ureter under the influence of hydrostatic pressure, assisted by contractions of muscles located within the walls (lining) of the ureter. Some patients experience a urological condition known as ureteral blockage or obstruction. Some common causes of ureteral blockage are the formation of tumors or abnormalities within the ureteral lining, or the formation and passage of kidney stones.

Ureteral stents are used to facilitate urinary drainage from the kidney to the bladder in patients having a ureteral obstruction or injury, or to protect the integrity of the ureter in a variety of surgical manipulations. Stents may be used to treat or avoid ureter obstructions (such as ureteral stones or ureteral tumors) which disrupt the flow of urine from the kidneys to the bladder. Serious obstructions may cause urine to back up into the kidneys, threatening renal function. Ureteral stents may also be used after endoscopic inspection of the ureter.

Ureteral stents typically are tubular in shape, terminating in two opposing ends: a kidney distal end and a bladder proximal end. One or both ends of a ureteral stent may be coiled in a spiral, pigtail or hook-type J-shape to prevent the upward and/or downward migration of the stent due, for example, to physiological movements. A kidney end coil is designed to retain the stent within the renal pelvis and to prevent stent migration down the ureter. The bladder end coil sits in the bladder and is designed to prevent stent migration upward toward the kidney. The bladder coil is also used to aid in retrieval and removal of the stent.

Unfortunately, certain drawbacks are inherent with these types of ureteral stents. For example, the extraneous material associated with the coiled ends of the stent can be an irritant to the patient, particularly in the trigone area. This trigonal irritation can be exacerbated, for example, by kidney motion relative to stent placement. Even normal breathing activity of a patient can result in significant kidney motion, on the order of 2–4 centimeters, resulting in irritation and discomfort for the patient.

What is needed is a ureteral stent with a bladder end design and connection method that prevents stent migration towards the kidney, does not irritate the trigone area of the bladder, does not create patient discomfort during routine motion of the bladder or kidney, and that prevents urine reflux up the ureter during bladder voiding.

SUMMARY OF THE INVENTION

One aspect of the present invention is directed to an expandable ureteral stent comprising an elongated member, a proximal retention structure, and a resilient portion connecting them. Each of these has a lumen, the lumens being in fluid communication with each other. The resilient portion allows the proximal retention structure to slideably move in relation to the proximal end of the elongated member between an expanded position and a retracted position.

In embodiments of the invention, the retention structure can comprise a nonlinear shape, a horn shape, a spherical shape, a mushroom shape, or a flared shape. The outer dimension of the proximal retention structure is larger than the outer diameter of the elongated member, to prevent entry of the proximal retention structure into the intramural tunnel.

In another embodiment, a stricture is disposed within one of the lumens to minimize urine reflux. The stricture can comprise an orifice in the proximal retention structure.

The resilient portion can comprise an elastomeric sleeve. The elastomeric sleeve can be disposed internally or externally relative to the elongated member. Additionally, it can be partially contained within the lumen of the elongated member when the proximal retention structure is in a retracted position. The resilient portion can also comprise a spring, and the spring can be biased toward the retracted position of the stent. The spring can be integrally formed with the proximal retention structure.

In some embodiments of the invention, the proximal retention structure is slideably moveable within the lumen of the elongated member. A retaining device can be used to prevent separation of the proximal retention structure and the elongated member. This retaining device can be a circumferential flange.

In some embodiments the stent comprises a distal retention structure. This distal retention structure defines a lumen, which is in fluid communication with the lumen of the elongated member. There can be an opening in the distal retention structure to allow drainage into its lumen.

In yet another aspect, the invention features an apparatus for positioning a ureteral stent having a retention structure with a nonlinear shape and a resilient portion, the apparatus comprising a guide wire and a pusher. The shape of the distal end of the pusher conforms to the shape of the retention structure of the stent, which can be a nonlinear shape, a horn shape, a spherical shape, a mushroom shape, or a flared shape. The pusher travels along the guide wire. The guide wire passes through the resilient portion of the stent.

In another aspect, the invention features a method of facilitating urinary drainage from a kidney to a bladder in a patient that reduces discomfort to the patient, comprising positioning a ureteral stent having an elongated member, a retention structure, and a resilient portion in the ureter of a a patient, and allowing the retention structure to slideably move relative to the elongated member, based on positioning of organs with the patient, including the kidney and bladder, or the breathing pattern of the patient. The resilient portion can be biased to a retracted position.

Another aspect of the invention features a method of manufacturing an adjustable stent. This comprises the steps of providing an elongated member, a retention structure and a resilient portion, and connecting the elongated member and the retention structure to opposing ends of the resilient portion. The resilient portion can include a coiled spring, which can be formed by an extrusion process. Heat forming techniques can be used to connect the resilient portion, or it can be integrally formed with the elongated member or the retention structure. A circumferential flange can be used to retain the spring.

BRIEF DESCRIPTION OF THE DRAWINGS

The foregoing discussion will be understood more readily from the following detailed description of the invention, when taken in conjunction with the accompanying drawings, in which:

FIGS. 2A and 2B show details of one embodiment of the invention;

DETAILED DESCRIPTION

Figure 1:
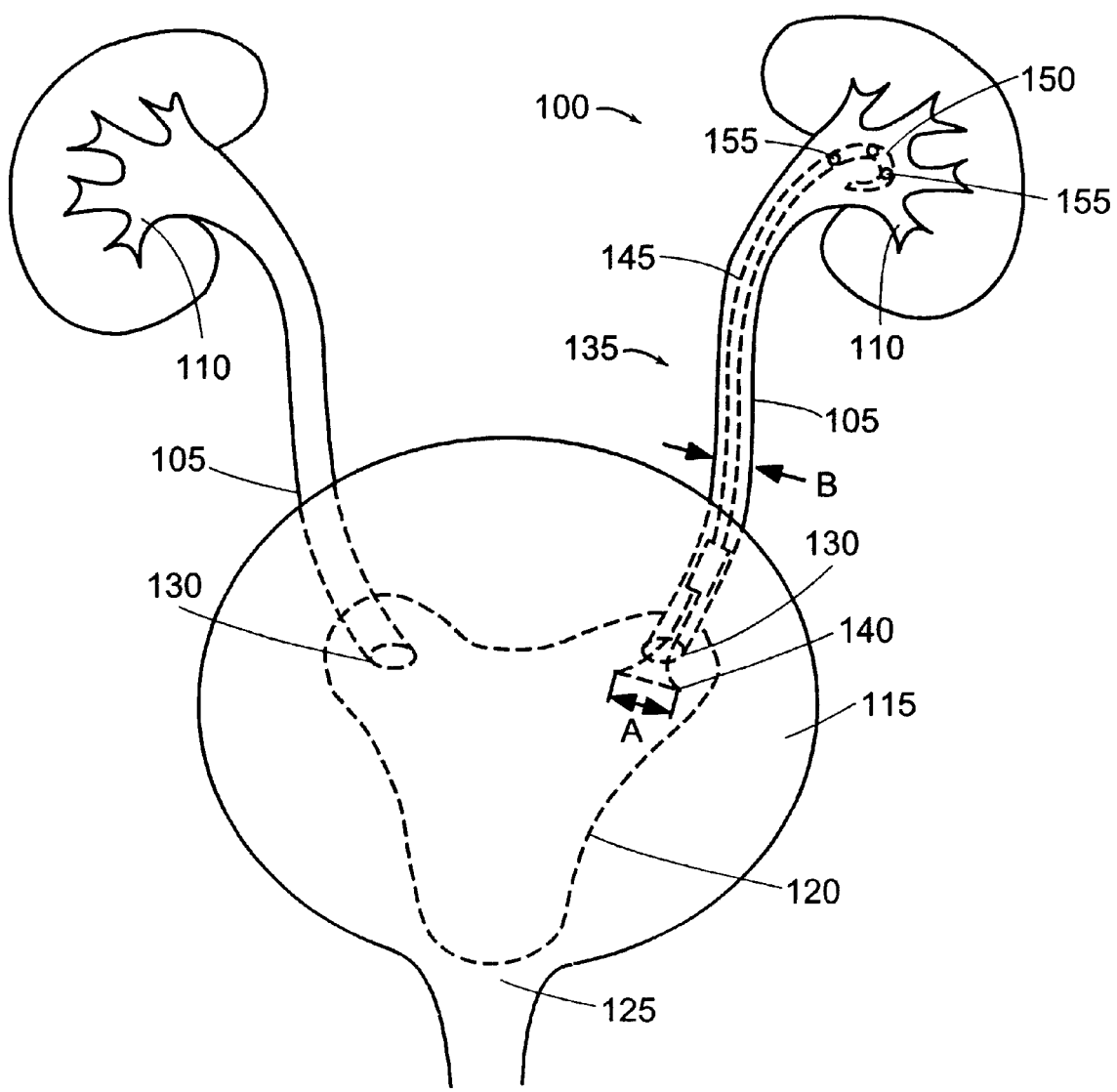
FIG. 1 is a schematic view of a human urinary tract, illustrating the placement of one embodiment of the invention within the ureter of a patient.

The invention features ureteral stents that, when positioned within the ureter of a patient, significantly reduce discomfort to the patient. Referring to the drawings, FIG. 1 illustrates a schematic view of a human urinary tract 100. The ureters 105 transport urine from the kidneys 110 to the bladder 115. When one or both of the ureters 105 become blocked or obstructed due to, for example, post kidney stone fragmentation/removal and ureteral stricture therapy, fluid drainage can become restricted. Ureteral stents are medical devices that are implanted within a ureter 105 to restore patency and fluid drainage.

Conventional ureteral stents have spiral, pigtail, or hook ends designed to retain the stent within the ureter. In the bladder, this type of retention structure contacts the bladder lining within a sensitive area known as the trigone 120. The trigone 120 is a generally triangular section of the bladder 115 located between the urethral opening 125 and the two ureteral orifices 130. The trigone 120 is a sensitive region of the bladder containing a nerve bed. Foreign objects within the trigone, such as the coiled end of a conventional ureteral stent, rubbing against the bladder, can stimulate this nerve bed and cause the patient to experience urinary urgency sensations. Stimuli within the trigone due to contact with the bladder end portion of conventional stents are also believed to be the source of patient discomfort. The ureteral stents of the invention provide an increase in comfort for a patient, in part, because the proximal retention structure 140 located at the bladder-end of the ureteral stent is designed to minimize stimulation in the trigone.

FIG. 1 illustrates the placement of one embodiment of the invention within the urinary tract of a patient. The ureteral stent 135 is located within the ureter 105 of a patient, with the distal retention structure 150 in the pelvis of the kidney, and the proximal retention structure 140 in the bladder. A lumen extends within the proximal retention structure 140, the elongated member 145, and the distal retention structure 150, to provide for the passage of fluid.

The proximal retention structure 140, elongated member 145, and distal retention structure 150 can be fabricated of materials such as nylon, polyurethane, or the like. Heat bonding of these materials is conveniently accomplished, for example, using an RF heat source as is commonly employed for plastic tubes and catheters. The desired shape of the proximal retention structure can be formed by injection molding or extrusion. It can also be heat-formed, for example, by flaring the working piece over an anvil of the appropriate shape, with the application of heat. Creation of a coiled or spiral shape of the distal retention structure can also be conveniently accomplished using heat formation techniques. Stent components suitable for use in the urinary tract of a patient are conveniently formed by these methods.

In use, the proximal retention structure 140 of the stent resides in the bladder 115 and can have a horn shape to minimize stimulation of the nerves within the trigone. In this embodiment, the horn shape of the proximal retention structure 140 flares or curves away from the trigone 120, to reduce patient discomfort. The shape of the proximal retention structure provides the ureteral stent of the invention with a broad surface that gently contacts the ureteral orifice 130, near the trigone. To minimize patient discomfort, the proximal retention structure contacts only this area, and does not contact other portions of the trigone or of the bladder surface. This is achieved in part due to the reduced size of the proximal retention structure, as compared with conventional spiral retention devices. The smaller size of the proximal retention structure of the invention makes it less likely that edges of the horn shape will contact the trigone or bladder surface during patient movement, or when the bladder and kidney move with respect to each other. Nevertheless, the size of the proximal retention structure is still sufficient to provide for effective grasping of the stent, for removal through a scope.

The largest diameter of the proximal retention structure 140, illustrated as dimension A in FIG. 1, should be greater than the diameter of the ureter 105, illustrated as dimension B in FIG. 1. This stabilizes the positioning of the stent 135 by preventing the stent from migrating toward the kidney 110. Moreover, the stent 135 can include a distal retention structure 150, such as the coil shape shown in FIG. 1. A lumen is disposed within the distal retention structure to provide for the passage of fluid. Additionally, the distal retention structure can have one or more openings 155 to facilitate the entry of fluid into the stent 135. The openings 155 can be positioned at or near the distal end of the stent, as shown in FIG. 1.

FIGS. 2A and 2B show additional details of an embodiment of the invention. In FIG. 2A, a resilient portion 205 is disposed between the proximal retention structure 140 and the elongated member 145. Incorporation of the resilient portion into the invention is intended to minimize patient discomfort, by providing a gentle biasing force that tends to draw the proximal retention structure 140 and the elongated member 145 toward each other. This bias limits the amount of force that is applied to the trigone 120 by the proximal retention structure 140. For example, even normal breathing activity of a patient can result in significant motion of the kidney 110 with respect to the bladder 115, on the order of 2–4 centimeters. The resilient portion 205 allows movement of the proximal retention structure 140 with respect to the elongated member 145 and the distal retention structure 150 (if a distal retention structure is present). As a patient inhales and the bladder moves away from the kidney, the overall length of the stent 135 increases as the resilient portion 205 expands. Conversely, as the patient exhales the resilient portion can contract, thereby maintaining a gentle and consistent positioning force of the proximal retention structure 140 with respect to the ureteral orifice 130. Thus, the ureteral stent of the invention compensates for the breathing pattern of the patient.

Another advantage of the resilient portion pertains to stent size. By judicious selection of the size and material of the resilient portion, the invention allows a wide range of useable stent lengths to be achieved by a single stent. In one embodiment, a stent-length variation of 5–8 centimeters can be achieved. This "one-size-fits-all" approach reduces the stent inventory that must be maintained by a surgical facility, since one type of stent can accommodate a wide variety of patient sizes. The resilient portion allows placement of the proximal retention structure near the intramural tunnel, while using the same type of stent for a range of patient sizes.

The resilient portion 205 comprises a lumen 210. The lumens of the proximal retention structure 215, the resilient portion 210, the elongated member 220, and the distal retention structure 225 (if a distal retention structure 150 is present), are all in fluid communication with each other, allowing drainage of fluid from the kidney 110 to the bladder 115. As illustrated, the distal retention structure can include multiple openings 155, to facilitate entry of fluid into the stent 135.

In one embodiment, the stent 135 includes a stricture 240. Although shown in FIG. 2A as located within the elongated member 145, the stricture can be located within any of the lumens (210, 215, 220, or 225) described above. Alternatively, the stricture can be positioned as an orifice, at an end of one of the lumens. The stricture reduces reflux up the ureter during a high bladder condition (voiding) by providing a restriction to flow, thereby reducing patient discomfort.

Figure 3A:
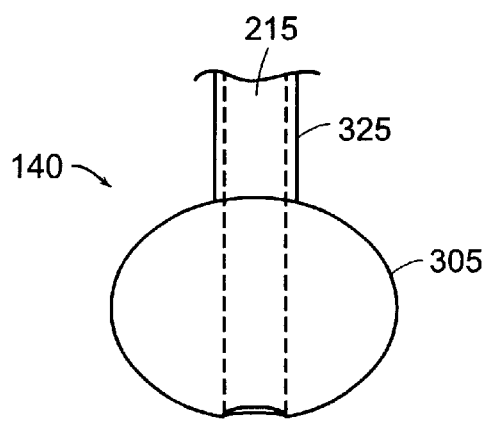
FIGS. 3A–3D show the shape of different embodiments of the proximal end of the ureteral stent of the invention.
Figure 3B:
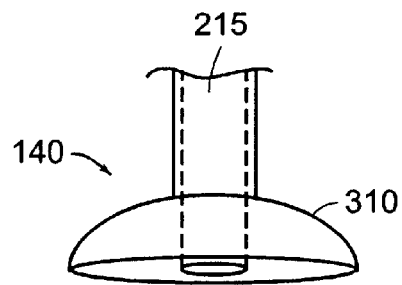
Figure 3C:
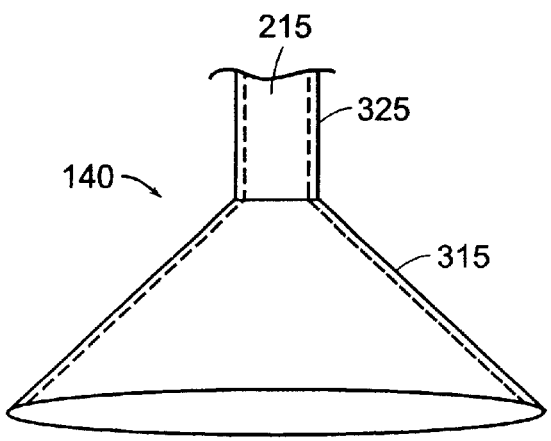
Figure 3D:
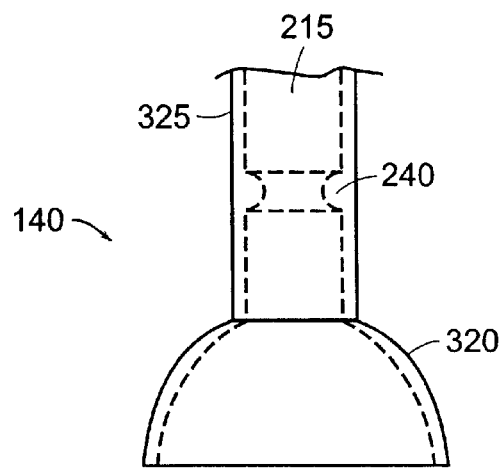

FIG. 2B shows an enlarged view of a horn-shaped embodiment of the proximal retention structure 140, including the lumen 215 within the proximal retention structure. Other embodiments of the proximal retention structure 140 are shown in FIGS. 3A–3D. For example, use of a spherical shape 305, a mushroom shape 310, a flared shape 315, an open-bowl shape 320, a triangular shape, or a hemispherical shape can all yield satisfactory results. In general, any nonlinear shape is considered to be within the scope of the invention. Each embodiment provides the advantages listed above. Contact with the trigonal area of the bladder is minimized, and stent position is maintained. These embodiments of the proximal retention structure comprise a trunk 325. The trunk of the proximal retention structure 140 comprises lumen 215, and is in communication with the resilient portion 205. As discussed above, a stricture 240 can be conveniently and effectively included in the lumen 215 of any of these embodiments of the proximal retention structure 140. The embodiment shown in FIG. 3D illustrates placement of the stricture 240 within the portion of the lumen 215 that is located in the trunk 325.

FIGS. 4–8 illustrate different embodiments and configurations of the resilient portion 205 of the invention, and different ways the proximal retention structure 140 can interact with the elongated member 145. The material of which the resilient portion can be a resilient material. The resilient material can be elastomeric, and this elastomeric property can provide a gentle biasing force towards the retracted position of the stent as it stretches and contracts. Elastomeric materials of various sizes, shapes, and materials are suitable for this purpose. The resilient portion can be made of TPR rubber, sometimes known as thermoplastic rubber, or of Kraton® (registered trademark of Shell Oil Company). Other elastomers are also suitable. Elastomers with melting temperatures similar to TPR or Kraton® are also particularly suitable, as they work especially well with the fabrication techniques discussed below.

When the resilient portion 205 comprises an elastomeric material, fabrication is conveniently accomplish by heat-attaching the elastic material to the proximal retention structure 140, and/or to the elongated member 145. The heat bonding is most effective when the members being joined have approximately the same melting temperature.

Although embodiments of the resilient portion comprising an elastomeric material are detailed below, other materials can be used for this purpose. An objective is to provide a material that provides a biasing force between the elongated member 145 and the proximal retention structure 140. Materials with shape memories work well for this purpose, as do combinations of materials that provide a shape memory. As an example, the resilient portion can be fabricated from superelastic materials, comprising metal alloys. Materials with superelastic properties make it possible to configure a component into a particular shape, such as a coil or a sleeve, and then modify reversibly the geometry of the component, such as by straightening it out. Once the device is straightened, after removal of the straightening force, the component reverts spontaneously to its predetermined configuration, thereby regaining its former geometry. In so doing, the component provides a biasing force back to its original configuration.

Superelastic materials can comprise alloys of In—Ti, Fe—Mn, Ni—Ti, Ag—Cd, Au—Cd, Au—Cu, Cu—Al—Ni, Cu—Au—Zn, Cu—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn. Preferably, the superelastic material comprises a nickel and titanium alloy, known commonly as nitinol available from Memry Corp. of Brookfield, Conn., or SMA Inc. of San Jose, Calif. The ratio of nickel and titanium in nitinol may be varied. Examples include a ratio of about 50% to about 52% nickel by weight, or a ratio of about 47% to about 49% nickel by weight. Nitinol has shape retention properties in its superelastic phase.

Figure 4:
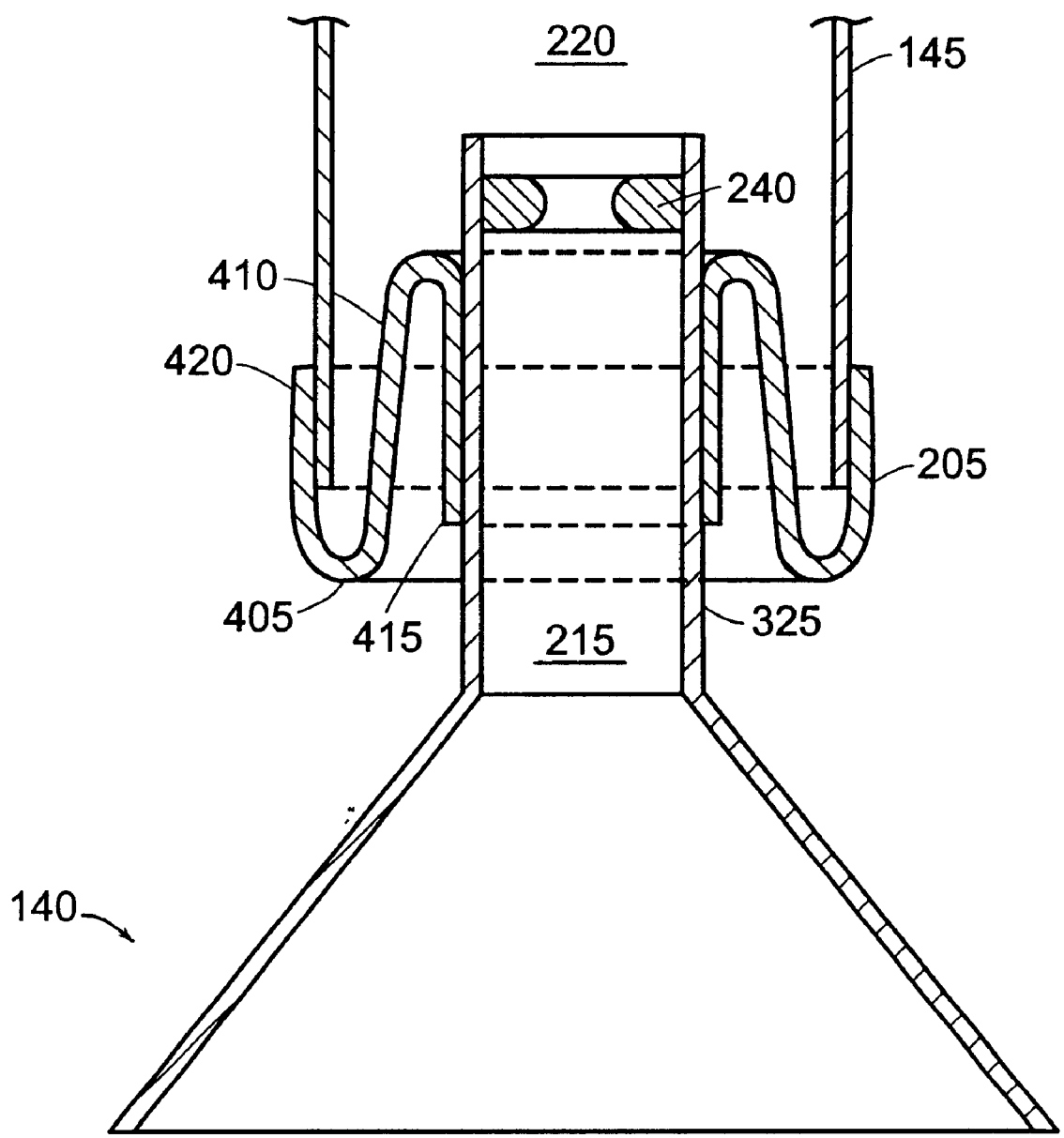
FIGS. 4–8 show different embodiments of the resilient portion of the invention.

Referring to FIG. 4, the resilient portion 205 can comprise an elastomeric material. The resilient portion comprises an outer surface 405 and an inner surface 410. It has a proximal end 415 and a distal end 420. As the proximal retention structure 140 and the elongated member 145 move away from each other to an expanded position, the resilient portion 205 stretches. The proximal end of the resilient portion 415 is attached to the trunk 325 of the proximal retention structure 140, and remains near the bladder 115. The distal end of the resilient portion 420 remains attached to the elongated member 145, and is drawn toward the kidney 110 during expansion of the stent. The resilient portion 205 is coupled with the proximal retention structure 140 and the elongated member 145 at all times. The lumen of the proximal retention structure 215, the lumen of the resilient portion 210, the lumen of the elongated member 220, and the lumen of the distal retention structure 225 (if a distal retention structure is present) remain in fluid communication with each other at all times providing for the drainage of fluid.

The resilient portion of the invention gently draws the elongated member and the proximal retention structure back to a retracted position, as any opposing forces allow. In this way, the resilient portion can provide a gentle biasing force towards the retracted position, allowing the stent to compensate for normal changes in organ location while minimizing discomfort to the patient. The biasing force between the proximal retention structure and the elongated member can be provided by a resilient portion that is fabricated from an elastomeric material.

The inner surface of both the distal end and proximal end of the resilient portion 205 of FIG. 4 is connected to the outer surface of the elongated member 145 and to the outer surface of the trunk 325 of the proximal retention structure 140, respectively. When in the retracted position, the resilient portion 205 is partially contained within the lumen of the elongated member 220. In this fashion, the lumen of the elongated member guides the trunk of the proximal retention structure 325 as it slides between retracted and expanded positions. The proximal retention structure 140 is free to move longitudinally with respect to the elongated member 145, although the resilient portion 205 provides a gentle biasing force towards the retracted position.

Figure 5:
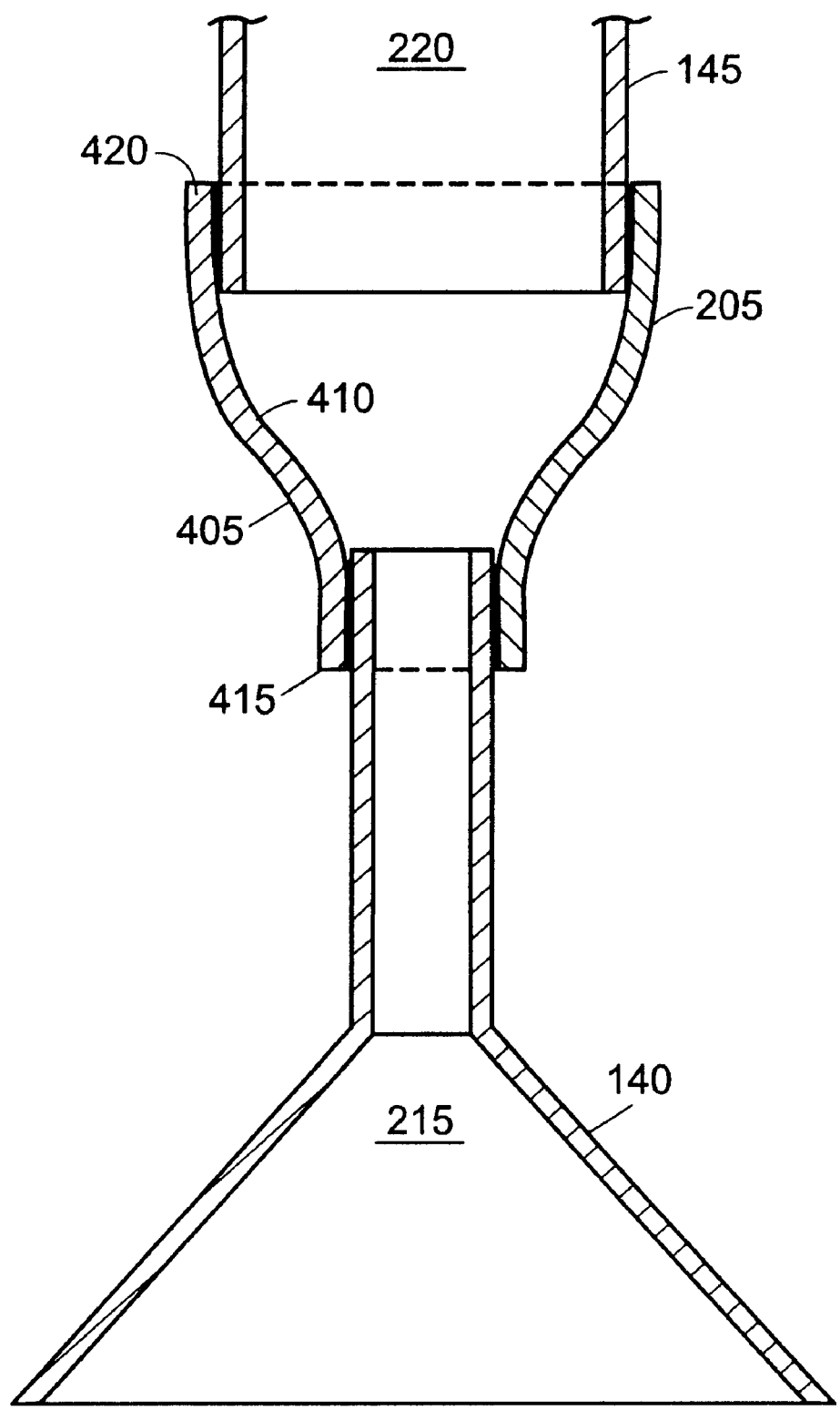

The proximal retention structure of FIG. 4 is shown in a mostly retracted configuration. As shown in this figure, a stricture 240 can be disposed within the lumen of the proximal retention structure 215 to reduce reflux up the ureter during a high bladder condition (voiding), by providing a restriction to flow. This stricture can also be located in other places, such as the lumen of the elongated member 220. FIG. 5 shows the resilient portion 205 of FIG. 4 with the proximal retention structure in an expanded position. In the absence of opposing forces, the resilient portion 205 draws the proximal retention structure 140 to the retracted position as illustrated in FIG. 4, thereby minimizing contact with the trigone 120.

Figure 6:
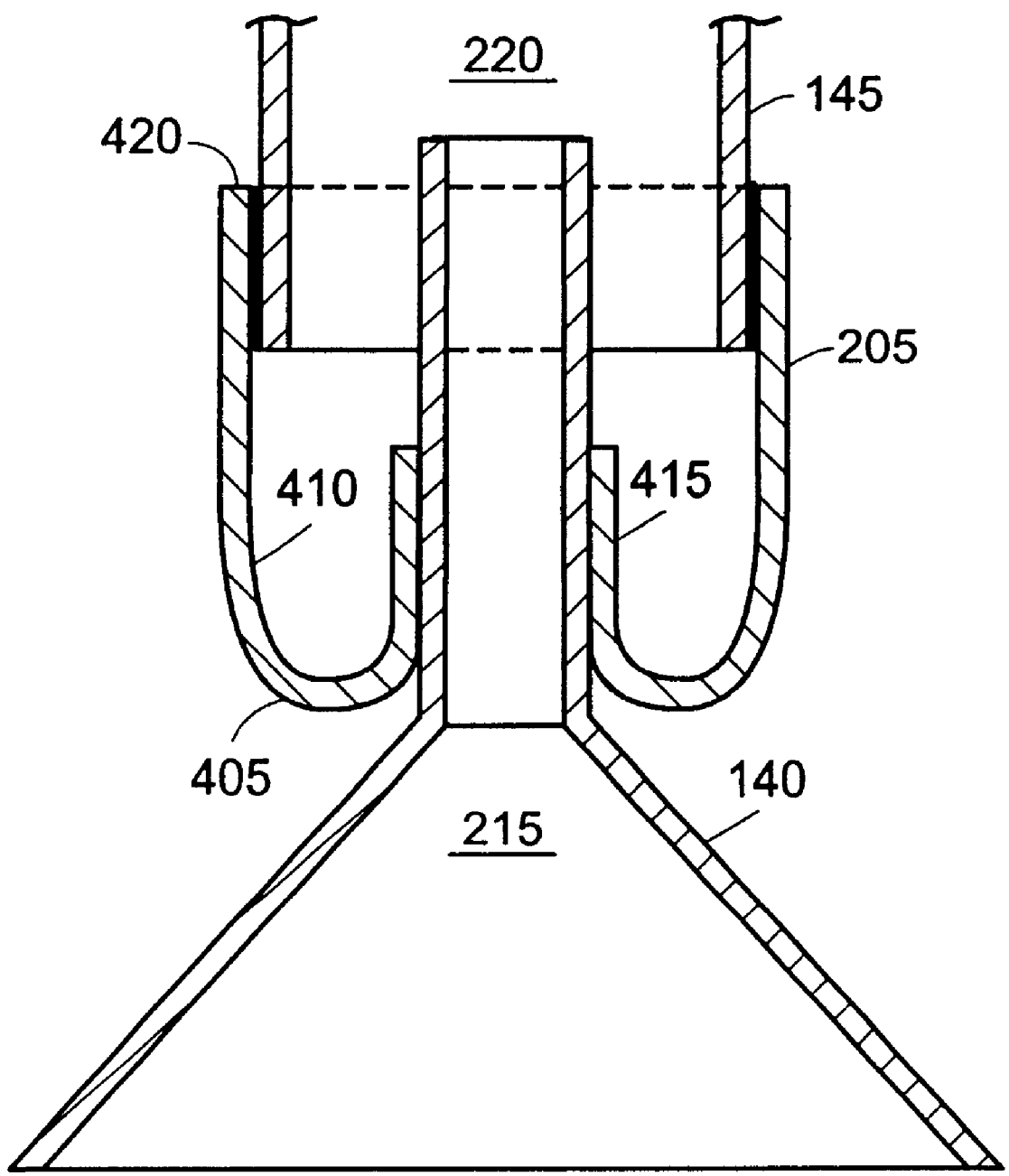

FIG. 6 shows another embodiment of the resilient portion 205. In this embodiment, the inner surface 410 of the distal end of the resilient portion 420 is connected to the outer surface of the elongated member 145, and the outer surface 405 of the proximal end of the resilient portion 415 is connected to the outer surface of the trunk 325 of the proximal retention structure 140, but the curvature of the resilient portion is reversed. Again, the trunk of the proximal retention structure can be contained within the lumen of the elongated member 220, but without the proximal end of the resilient portion 415 entering this lumen 220. The material of the resilient portion can be elastomeric, and this elastomeric property can provide a gentle biasing force towards the retracted position of the stent. The proximal retention structure 140 is free to move longitudinally with respect to the elongated member 145, between retracted and expanded positions. Although not shown, a stricture can be disposed within the lumen of the elongated member 220, or within the lumen of the proximal retention structure 215, to reduce reflux up the ureter during a high bladder condition (voiding), by providing a restriction to flow.

Figure 7:
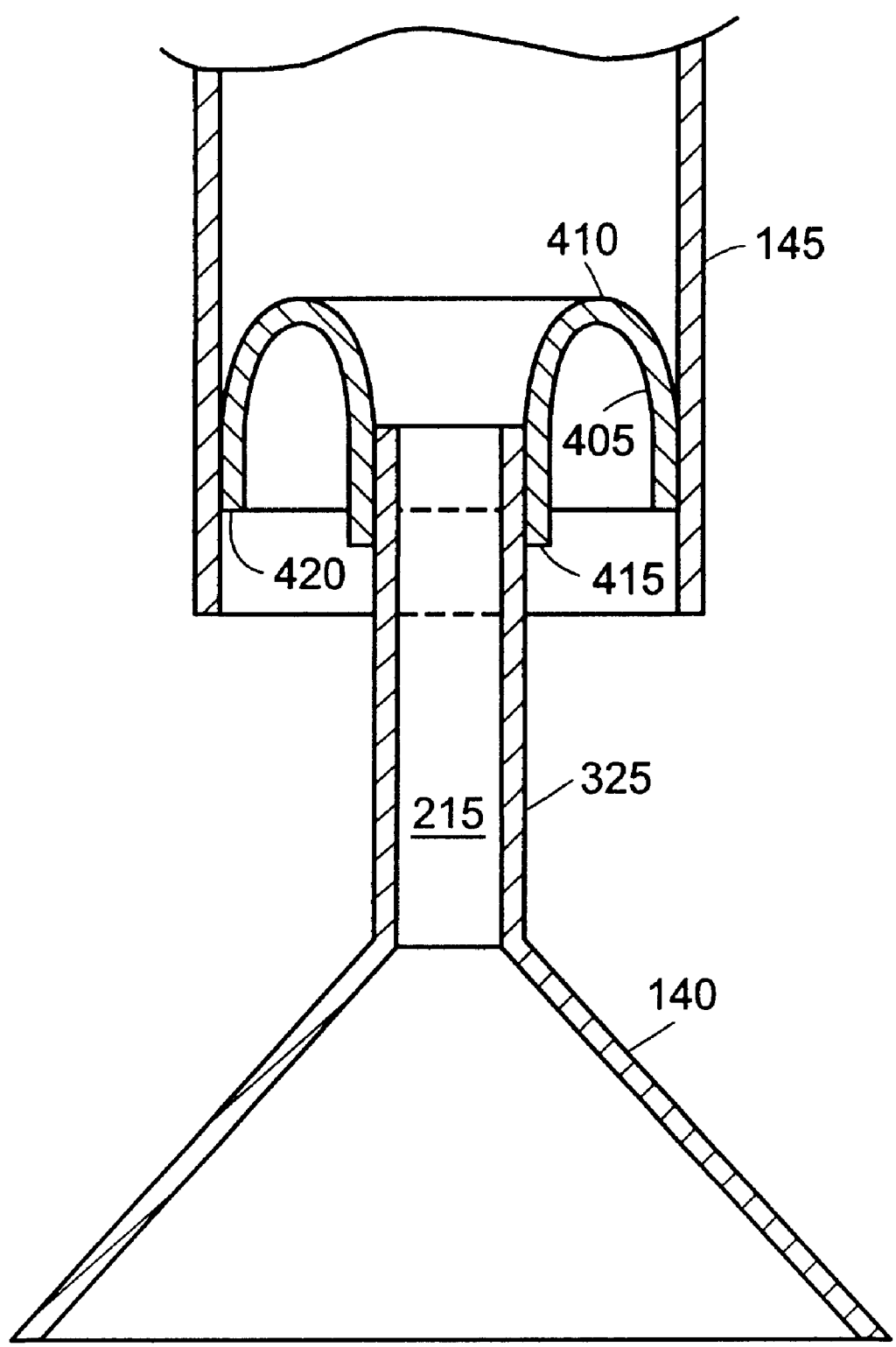

FIG. 7 shows another embodiment of the resilient portion 205. Here, the inner surface 410 of both ends of the resilient portion are connected to the inner surface of the elongated member 145, and to the outer surface of the trunk of the proximal retention structure 325. As illustrated, the material of the resilient portion 205 is concave in the distal direction. However, it could be directed proximally. As indicated above, the material of which the resilient portion is made can be elastomeric, and this elastomeric property can provide a gently biasing force towards the retracted position of the stent. The proximal retention structure 140 is free to move longitudinally with respect to the elongated member 145, between retracted and expanded positions. In this embodiment, the trunk of the proximal retention structure can be disposed within the lumen of the elongated member. Although not shown, a stricture can be disposed within the lumen of the elongated member 220 or within the lumen of the proximal retention structure 215, to reduce reflux up the ureter during a high bladder condition (voiding), by providing a restriction to flow.

Figure 8:
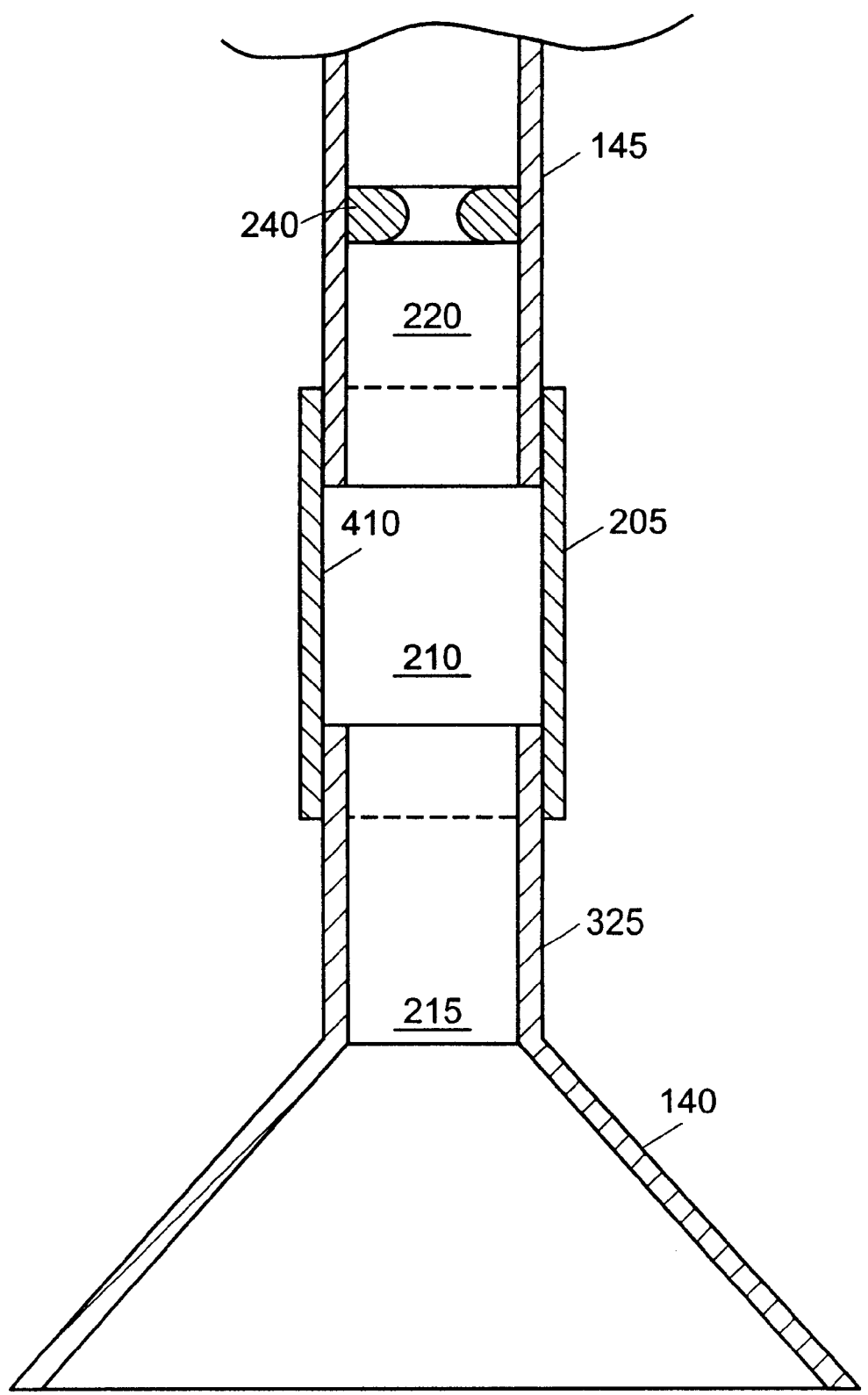

FIG. 8 shows yet another embodiment of the resilient portion 205. This embodiment illustrates that different configurations can exist between the diameter of the trunk of the proximal retention structure 325 and the diameter of the elongated member 145. In this embodiment, the two have the same diameter. FIG. 8 shows the inner surface of the resilient portion 410 connected to the outer surface of the elongated member 145 and to the outer surface of the proximal retention structure 140. The material of which the resilient portion is made can be elastomeric, and this elastomeric property can provide a gently biasing force towards the retracted position of the stent. The proximal retention structure 140 is free to slideably move with respect to the elongated member 145, between a retracted and expanded position. As illustrated in FIG. 8, the diameters of the trunk of the proximal retention structure 325 and the elongated member 145 are the same. Even though the trunk of the proximal retention structure cannot fit into the lumen of the elongated member, the stent can still alternate between an expanded and a retracted position. Any alignment required between the proximal retention structure 140 and the elongated member 145 is provided by the resilient portion 205.

Figure 9:
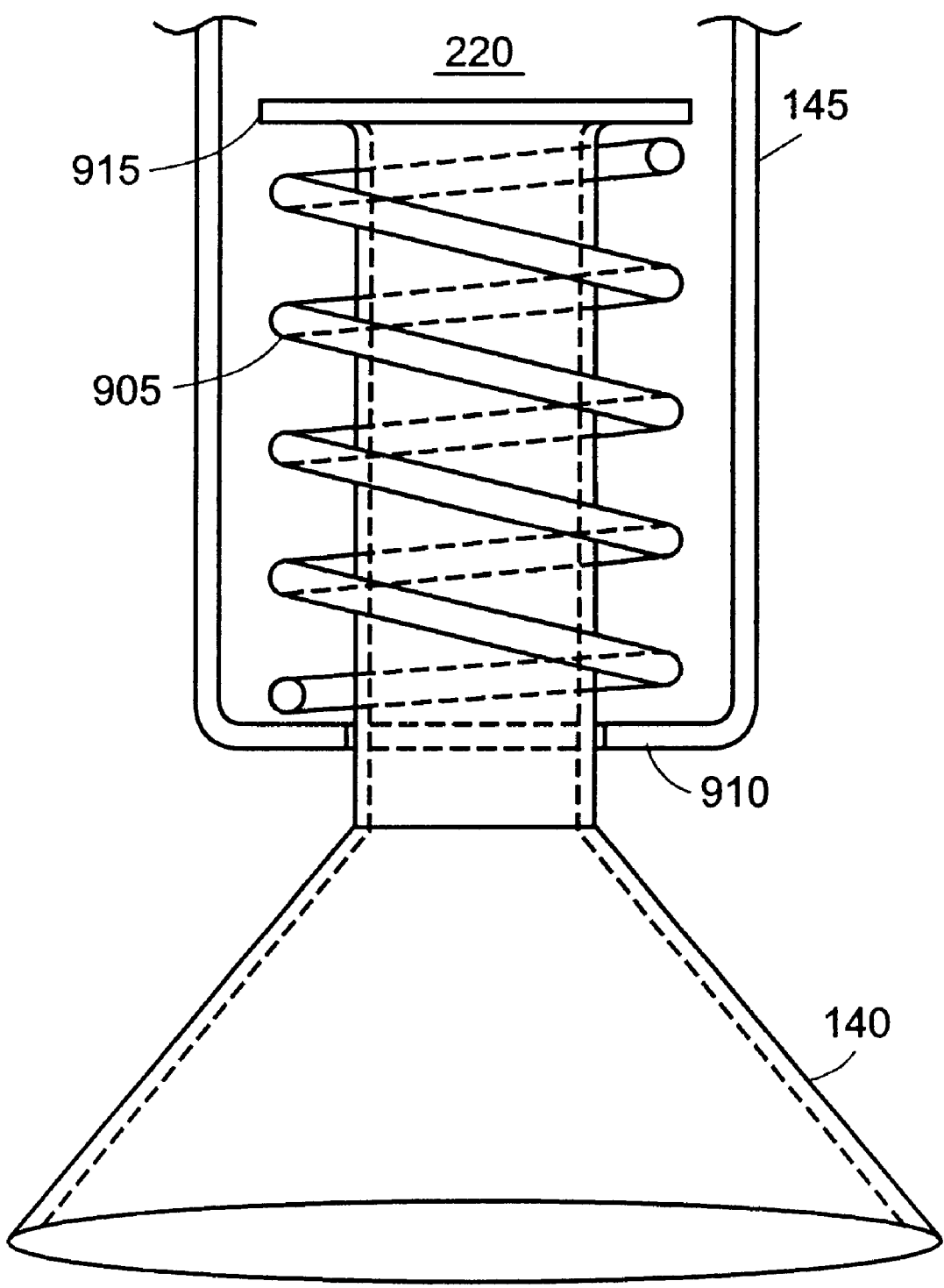
FIG. 9 shows yet another embodiment of the resilient portion of the invention, employing a spring-like device.

FIG. 9 shows a cutaway view of another embodiment of the resilient portion, comprising a coiled spring 905. The coiled spring is maintained between the circumferential flange 910 of the elongated member, and the circumferential flange 915 of the proximal retention structure. Not only do these flanges provide containment of the spring, but they also keep the proximal retention structure 140 from sliding out of the elongated member 145.

The coiled spring 905 can be formed by an extrusion process. Heat forming can be used to shape the coil. If the coiled spring 905 is integrally formed with the proximal retention structure 140, then one method of assembly and fabrication comprises inserting the circumferential flange of the proximal retention structure 915 into the proximal end of the elongated member 145, followed by using heat forming techniques to form the circumferential flange of the elongated member 910. This is easily accomplished by using heat to soften the proximal end of the elongated member, and partially folding the proximal portion of the elongated member in towards the lumen of the elongated member 220, to form the circumferential flange 910. Alternatively, if the coiled spring 905 and proximal retention structure 140 were not integrally formed together, they can be preassembled and then joined with the elongated member 145 using techniques similar to those described above.

The coiled spring 905 can be biased toward the retracted position of the stent. The elongated member 145 acts as a guide for the proximal retention structure 140, as it moves between retracted and expanded positions. The coiled spring can be a separate piece, or it can be integrally formed with the elongated member, for example, by integrally molding it at the time of manufacture of the elongated portion. Alternatively, it could be integrally molded with the proximal retention structure.

Figure 10:
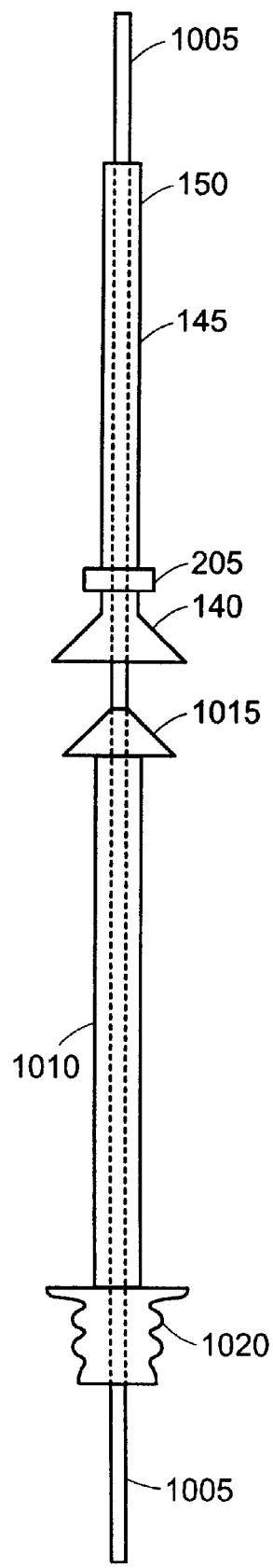
FIG. 10 is an illustration of a pusher device that can be used for positioning the ureteral stent of the invention.

In another aspect, the invention provides an apparatus for delivering the stent into a patient, as shown in FIG. 10. The delivery apparatus 1000 comprises a guide wire 1005 and a pusher 1010. The distal end of the pusher 1015 has a shape that is conformed to the shape of the proximal retention structure 140. For example, the distal end can conform to a spherical shape, a mushroom shape, a flared shape, a triangular shape, or a hemispherical shape. The proximal end of the pusher includes a grip 1020, to assist in using the device.

In use, the stent 135 is mounted on the delivery apparatus 1000, as shown in FIG. 10. The distal retention structure 150 (if a distal retention structure is present), is also threaded over the guide wire 1005, and most of its inherent curvature removed. Next, the guide wire is inserted into the bladder 115, through the ureteral orifice 130, up the ureter 105, and into the kidney 110. The pusher 1010 is then moved along the guide wire 1005, pushing the stent 135 along the guide wire 1005 towards the kidney 110. The proximal end of the elongated member can be positioned either at or distal to the ureteral orifice 130. The stent can also be positioned such that the resilient portion 205 is at or distal to the ureteral orifice 130.

Once the surgeon has achieved the desired positioning of the stent, the guide wire 1005 is removed, while holding the pusher 1010 stationary to maintain the stent 135 in position. Finally, pusher 1010 is removed from within the patient, leaving the stent 135 in place. Using this method, the stent of the invention can be precisely positioned within the ureter and bladder of the patient, and the proximal retention structure 140 can be accurately positioned at or near the trigonal area of the bladder. The method can also be used to accurately position the distal retention structure 150 (if a distal retention structure is present), within the kidney.

In one embodiment of the invention, the guide wire, pusher, and stent are inserted into the ureter 105 percutaneously through a surgical opening. In another embodiment, they are inserted into the ureter via the urinary tract of the patient.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A ureteral stent comprising:
   an elongated member defining a first lumen;
   a proximal retention structure defining a second lumen and disposed at a proximal end of the elongated member; and
   a resilient portion defining a third lumen in fluid communication with the first and second lumens, the resilient portion connected to the proximal retention structure and the proximal end of the elongated member so as to allow the proximal retention structure to slideably move in relation to the proximal end of the elongated member between a retracted position and an expanded position.

2. The ureteral stent of claim 1, wherein the proximal retention structure comprises a nonlinear shape.

3. The ureteral stent of claim 1, wherein the proximal retention structure comprises at least one of a horn shape, a spherical shape, a mushroom shape, or a flared shape.

4. The ureteral stent of claim 1, wherein an outer dimension of the proximal retention structure is larger than the diameter of the elongated member, to prevent entry of the retention structure into an intramural tunnel.

5. The ureteral stent of claim 1, further comprising a stricture disposed within one of the lumens, wherein a cross-sectional flow area of the stricture is less than that of any of the lumens.

6. The ureteral stent of claim 5, wherein the stricture defines an orifice in the proximal retention structure.

7. The ureteral stent of claim 1, wherein the resilient portion comprises a resilient material.

8. The ureteral stent of claim 1, wherein the resilient portion comprises an elastomeric material.

9. The ureteral stent of claim 1, wherein the resilient portion comprises a thermoplastic rubber.

10. The ureteral stent of claim 1, wherein the resilient portion is biased to the retracted position.

11. The ureteral stent of claim 1, wherein the resilient portion is expandable and retractable to allow the proximal retention structure and the elongated member to move to the expanded position and the retracted position.

12. The ureteral stent of claim 1, wherein the resilient portion comprises an elastomeric sleeve.

13. The ureteral stent of claim 1, wherein in the retracted position of the stent, the resilient portion is partially disposed within the first lumen.

14. The ureteral stent of claim 1, wherein the resilient portion is disposed within the elongated member.

15. The ureteral stent of claim 1, wherein the resilient portion is disposed external to the elongated member.

16. The ureteral stent of claim 1, wherein the resilient portion comprises a spring biased to the retracted position of the stent.

17. The ureteral stent of claim 16, wherein the spring is integrally formed with the proximal retention structure.

18. A ureteral stent comprising:
    an elongated member defining a first lumen:
    a proximal retention structure defining a second lumen and disposed at a proximal end of the elongated member: and
    a resilient portion defining a third lumen in fluid communication with the first and second lumens, the resilient portion connected to the proximal retention structure and the proximal end of the elongated member so as to allow the proximal retention structure to slideably move in relation to the proximal end of the elongated member between a retracted position and an expanded position, such that the proximal retention structure is slideably moveable within the first lumen of the elongated member.

19. The ureteral stent of claim 1, further comprising a retaining device to prevent separation of the proximal retention structure and the elongated member.

20. The ureteral stent of claim 19, wherein the retaining device comprises a circumferential flange.

21. The ureteral stent of claim 1, further comprising a distal retention structure defining a fourth lumen in fluid communication with the first lumen.

22. The ureteral stent of claim 21, further comprising an opening in the distal retention structure, wherein the opening is in fluid communication with the fourth lumen and provides for the drainage of a fluid into the fourth lumen.

23. A ureteral stent having a resilient portion and a retention structure with a nonlinear shape, and an apparatus for positioning the stent, comprising:
    the ureteral stent comprising an elongated member, the resilient portion in communication with the retention structure and the elongated member, such that the resilient portion allows the retention structure to slideably move relative to the elongated member between an expanded position and a retracted position,
    a guide wire positionable within a ureter ,wherein the guide wire passes through the resilient portion; and
    a pusher disposed about the guide wire to travel along the guide wire, wherein a shape of a distal end of the pusher conforms to the nonlinear shape of the retention structure to position the stent within the ureter.

24. The apparatus of claim 23, wherein the nonlinear shape of the retention structure comprises at least one of a horn shape, a spherical shape, a mushroom shape, or a flared shape.

25. A method of facilitating urinary drainage from a kidney to a bladder in a patient that reduces discomfort to the patient, comprising:
    positioning a ureteral stent in a ureter of a patient, the ureteral stent having an elongated member, a retention structure, and a resilient portion in communication with the retention structure and the elongated member; and
    allowing the retention structure to slideably move relative to the elongated member between an expanded position and a retracted position, based on at least one of: relative positioning of organs within the patient, a breathing pattern of the patient, or positions of the kidney and the bladder.

26. The method of claim 25, wherein the organs comprise the kidney and the bladder.

27. The method of claim 25, wherein the organs are the kidney and the bladder.

28. The method of claim 25, wherein the allowing step comprises providing a resilient portion biased to the retracted position.

29. The method of claim 25, further comprising the step of utilizing the resilient portion to facilitate the step of allowing the retention structure to slideably move relative to the elongated member.

30. A method of manufacturing an adjustable ureteral stent, comprising the steps of:

providing an elongated member, a retention structure, and a resilient portion biased to slideably move between contracted and expanded states; and connecting at least one of the elongated member or the retention structure to an end of the resilient portion.

31. The method of claim 30, wherein the resilient portion comprises a coiled spring.

32. The method of claim 31, wherein the coiled spring is formed by an extrusion process.

33. The method of claim 31, further comprising the step of providing at least one circumferential flange to retain the spring.

34. The method of claim 30, wherein the connecting step includes using heat-forming techniques.

35. The method of claim 30, wherein the resilient portion is integrally formed with at least one of the elongated member or the retention structure.

* * * * *